United States Patent
Roemburg et al.

(10) Patent No.: US 9,586,228 B2
(45) Date of Patent: Mar. 7, 2017

(54) ATOMISER SYSTEM

(71) Applicant: AIR AROMA RESEARCH PTY LTD, Victoria (AU)

(72) Inventors: Johan Van Roemburg, Brighton (AU); Derk Reilink, Ultrecht (NL); Petrus Henricus Aloysius Nicolaus Kuhn, Heiligenschwendi (CH)

(73) Assignee: AIR AROMA RESEARCH PTY LTD, Victoria (AU)

( * ) Notice: Subject to any disclaimer, the term of this patent is extended or adjusted under 35 U.S.C. 154(b) by 334 days.

(21) Appl. No.: 14/396,590

(22) PCT Filed: Apr. 18, 2013

(86) PCT No.: PCT/AU2013/000408
§ 371 (c)(1),
(2) Date: Oct. 23, 2014

(87) PCT Pub. No.: WO2013/159142
PCT Pub. Date: Oct. 31, 2013

(65) Prior Publication Data
US 2015/0076716 A1   Mar. 19, 2015

(30) Foreign Application Priority Data

Apr. 23, 2012  (AU) ................. 2012901604

(51) Int. Cl.
*B05B 17/06* (2006.01)
*B05B 17/00* (2006.01)
(Continued)

(52) U.S. Cl.
CPC ...... *B05B 17/0653* (2013.01); *B05B 17/0646* (2013.01); *B05B 17/0684* (2013.01);
(Continued)

(58) Field of Classification Search
CPC . A61L 9/122; A61L 9/127; A61L 9/14; A61L 2209/132; A61L 2209/133;
(Continued)

(56) References Cited

U.S. PATENT DOCUMENTS 3,587,968 A * 6/1971 Hennart et al. ........... A61L 9/12
239/309
5,000,383 A * 3/1991 van der Heijden . A01M 1/2044
239/44
(Continued)

FOREIGN PATENT DOCUMENTS

FR   2929861   10/2009
GB   2440516   2/2008
(Continued)

OTHER PUBLICATIONS

International Searching Authority, "Search Report", issued in connection with PCT patent application No. PCT/AU2013/000408, mailed on Jul. 12, 2013, 3 pages.
(Continued)

*Primary Examiner* — Charles Bushey
(74) *Attorney, Agent, or Firm* — Hanley, Flight & Zimmerman, LLC

(57) ABSTRACT

An atomizer system (2) comprising a fragrance cartridge (4) and a docking housing (6) in which the fragrance cartridge (4) is installed. The fragrance cartridge (4) including a bottle (8) for holding a liquid fragrance (10) therein; a wick (48) extending down into the bottle (8); a piezo disc (76) for atomizing the liquid fragrance (10) received from the wick (48); and an adjustable cap (98) by which a user activates the cartridge (4), bringing the liquid fragrance (10) into contact with a certain portion of the wick (48).

20 Claims, 16 Drawing Sheets

(51) Int. Cl.
  *H01L 41/09* (2006.01)
  *A61L 9/12* (2006.01)
  *A61L 9/14* (2006.01)

(52) U.S. Cl.
  CPC ............... *A61L 9/122* (2013.01); *A61L 9/127* (2013.01); *A61L 9/14* (2013.01); *A61L 2209/132* (2013.01); *A61L 2209/133* (2013.01); *H01L 41/0973* (2013.01)

(58) Field of Classification Search
  CPC ............ B05B 17/0646; B05B 17/0653; B05B 17/0684; H01L 41/0973
  USPC .............................. 261/81, 104, 107, DIG. 88
  See application file for complete search history.

(56) References Cited

U.S. PATENT DOCUMENTS

| | | | |
|---|---|---|---|
| 6,341,732 B1 * | 1/2002 | Martin | ................ B05B 17/0684 128/200.16 |
| 7,490,815 B2 * | 2/2009 | Tollens | ............... B05B 17/0646 261/30 |
| 7,547,004 B2 * | 6/2009 | Hsu | ........................... F24F 6/02 261/104 |
| 2005/0103891 A1 | 5/2005 | Abergel et al. | |
| 2005/0271371 A1 | 12/2005 | Wefler | |
| 2006/0120080 A1 | 6/2006 | Sipinski et al. | |
| 2008/0011874 A1 | 1/2008 | Munagavalasa et al. | |

FOREIGN PATENT DOCUMENTS

| | | |
|---|---|---|
| WO | 0197982 A1 | 12/2001 |
| WO | 2006110794 | 10/2006 |
| WO | 2009001319 A1 | 12/2008 |
| WO | 2009066329 A1 | 5/2009 |

OTHER PUBLICATIONS

International Searching Authority, "Written Opinion", issued in connection with PCT patent application No. PCT/AU2013/000408, mailed on Jul. 12, 2013, 4 pages.

* cited by examiner

ATOMISER SYSTEM

RELATED APPLICATIONS

This patent arises from the U.S. national stage of International Patent Application Serial No. PCT/AU2013/000408, having an International Filing Date of Apr. 18, 2013, and claims priority to Australian Patent Application No. 2012901604, which was filed on Apr. 23, 2012, both of which are hereby incorporated by reference in their entireties.

TECHNICAL FIELD

The present invention relates to systems for atomising a liquid. In a particular aspect, the invention relates to systems for atomising a liquid fragrance and or anti-bacterial or anti-viral liquids.

BACKGROUND ART

Any discussion of documents, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and broad consistory statements herein.

Fragrance systems are known to have been used to emit liquid fragrance into the surrounding room air. However, there have been some difficulties with prior constructions of fragrance systems.

For example, whilst not being an admission of common general knowledge, there are some fragrance devices which have a bottle filled with perfume liquid, a wick extending up through the bottle from its base, and a piezo disc with mesh at the top of the wick. The wick transports the perfume liquid in the bottle by capillary action up to the mesh of the piezo disc where the liquid perfume is atomised. At the start of the product life, when the bottle is full with liquid perfume, most of the length of the wick is immersed in the liquid perfume. This can cause the region of the piezo mesh in contact with the wick to become oversaturated or waterlogged, thereby preventing the piezo disc from diffusing the liquid perfume. Moreover, the oversaturation or waterlogging can lead to degeneration of the piezo disc soon after, and sometimes even prior to, purchase by a user, thereby shortening the life of the device and/or rendering it dysfunctional or useless. Thus, it may be advantageous to provide a new cartridge wherein the wetness of the piezo disc is regulatable, or the piezo disc remains dry until activation by a user.

Moreover, despite this problematic early degeneration of the piezo disc, there has been no solution allowing for replacement by a user. Thus, it may be advantageous to provide a system in which the cartridge containing the piezo disc is easily replaceable following disc degeneration.

Saturation of the mesh when the bottle is full with liquid perfume can also lead to excessive amounts of fragrance being atomised and emitted into the surrounding environment. On the other hand, as the liquid perfume is gradually consumed and the liquid level drops towards the base of the bottle, the opposite problem can arise where only a small surface area at the base of the wick is immersed in the liquid, thereby leading to excessive dryness of the piezo mesh and not enough liquid fragrance being atomised and emitted into the surrounding environment. Thus, it may be advantageous to provide a new cartridge in which the wetness of the piezo disc may be maintained at a consistent level as the liquid is consumed.

Another disadvantage associated with prior art systems includes poor spreading or wasting of the atomised fragrance when emitted into the room air. Thus, it may be advantageous to provide a system which improves spreading of emitted particles into the surrounding environment.

In light of the above, it may be advantageous to provide a new system, or new component for a system, which reduces, limits, overcomes, or ameliorates some of the problems, drawbacks, or disadvantages associated with prior art systems, or provides an effective alternative to such systems.

DISCLOSURE OF THE INVENTION

In one aspect the invention may provide an atomiser system comprising:
 a cartridge comprising,
  a container for containing a liquid,
  an atomising mechanism for atomising the liquid, the atomizing mechanism comprising a piezo member, and
  an electrical mechanism for connecting the atomising mechanism to an electrical power source.

The system may be adjustable to alter or maintain the wetness of the piezo member.

With the cartridge in a dry configuration, the supply of liquid to the piezo member may be inhibited, and with the cartridge in a wet configuration, supply of liquid to the piezo member may be enabled.

The piezo member may remain dry until the system is activated by a user.

The system may be adapted to maintain the piezo member at a substantially consistent wetness despite changes in cartridge orientation or liquid volume in the container.

The cartridge may be adjustable to alter the supply of liquid to the piezo member.

The cartridge may comprise a liquid supply mechanism for supplying the liquid to the atomising mechanism. The liquid supply mechanism may comprise a wick adapted to draw the liquid therealong. This may occur regardless of the orientation of the cartridge or wick.

The liquid may comprise a fragrance.

The atomising mechanism may comprise a piezo member. The piezo member may be adapted to contact the wick. In a suitable form the piezo member may be adapted to contact a top end of the wick.

The piezo member may comprise a piezo disc. The piezo member may comprise a mount on which the disc is mounted.

The piezo disc may be ring shaped. It may comprise ceramic material.

The mount may comprise a sheet. The sheet may comprise stainless steel mesh.

The cartridge may be adjustable between a non-use configuration and a use configuration.

The cartridge may comprise an adjustment mechanism for adjusting the cartridge between the non-use configuration and the use configuration.

The cartridge may be adjustable between a dry configuration and a wet configuration. The non-use configuration may comprise the dry configuration, and the use configuration may comprise the wet configuration.

In the dry configuration, the piezo member may be dry. This may be as a result of separation of the wick from the liquid.

In the wet configuration, the piezo member may be wet with liquid. This may be as a result of the liquid being in contact with a part of the wick.

The adjustment mechanism may comprise an unlockable or releasable cap. The cap may be unlocked or released by twisting thereof.

The adjustment mechanism may comprise an adjustment member, and a ramp on which the adjustment member slides. The adjustment member may be adapted to slide up the ramp during unlocking or release of the cap. There may be a plurality of adjustment members with corresponding ramps. These may be of various shapes and sizes.

The adjustment member may comprise a guide pin and an angled guide slot in which the pin is retained. The guide pin may slide up along the guide slot during unlocking or release of the cap. The guide pin and its corresponding guide slot may be located adjacent the adjustment member and ramp. There may be a plurality of guide pins and guide slots.

The cartridge may be adjustable between a non-vibrating configuration and a vibrating configuration. The non-use configuration may comprise the non-vibrating configuration, and the use-configuration may comprise the vibrating configuration.

In the non-vibrating configuration, the piezo member may not receive power from the electrical power source. Thus, the piezo member may remain still with respect to the wick and atomisation may not occur.

In the vibrating configuration, the piezo member may receive power from the electrical power source. This may cause the piezo member to vibrate, resulting in atomisation of the liquid when the piezo member is wet with the liquid.

In the non-vibrating configuration, the atomising mechanism may be unconnectable to the electrical power source. In the vibrating configuration, the atomising mechanism may be connectable to the electrical power source.

The cartridge may comprise an electrical contact. The electrical contact may comprise a circular ring shaped member.

The electrical contact may be concealed in the non-vibrating configuration and accessible in the vibrating configuration.

The piezo member may be in contact with the top end of the wick.

The piezo member may be arranged at an angle with respect to the wick.

The piezo member may be arranged at angle between 1 and 10 degrees off perpendicular with respect to the length or longitudinal axis of the wick. In a particular form, the piezo member may be arranged at approximately 5 degrees off perpendicular with respect to the length or longitudinal axis of the wick.

The piezo member may be arranged off centre with respect to the length or longitudinal axis of the wick.

The piezo member may be arranged off centre with respect to the top of the wick. Thus, the piezo member may be arranged more to one side at the top of the wick.

The piezo member may be arranged at an angle and off centre with respect to the length or longitudinal axis of the wick.

The cartridge may be placed in any orientation.

The wick may be placed in any orientation.

The wick may be adapted to draw liquid therealong regardless of the orientation of the cartridge or the wick.

The liquid supply mechanism may comprise an elastic member. The elastic member may be biased to urge a part of the wick against the piezo member. The elastic member may comprise a spring. Thus, the wick may be spring loaded.

The atomiser system may comprise a dock for the cartridge. The dock may comprise a housing.

The dock may comprise the electrical power source. The electrical power source may comprise a battery. In another form, the electrical power source may comprise an electrical socket connected to a mains power supply. In yet another form, the cartridge may comprise the electrical power source.

The dock may comprise an electrical retainer. The electrical retainer may be adapted to removably retain the cartridge in the dock, and electrically connect the retained cartridge to the power source. The electrical connection may be broken by removing the cartridge from the electrical retainer.

When retained in the dock, the electrical connection may be maintained regardless of the axial orientation of the cartridge. This may be due to the circular ring shaped member remaining in contact with the electrical retainer.

The dock may comprise a flow altering mechanism for altering the flow path of the atomised fragrance particles as they are emitted from the atomising system.

The flow altering mechanism may create an external air flow. The external air flow may be adapted to alter the flow path of the atomised fragrance particles by creating a pressure difference adjacent the emission of fragrance particles, thereby drawing the fragrance particles toward the external air flow.

The external air flow may be adapted to alter the flow path of the fragrance particles by pushing fragrance particles which pass into its flow stream.

The flow altering mechanism may comprise a fan duct for producing the external air flow. The flow altering mechanism may comprise an air aperture at the top of the housing, the air aperture being adjacent a fragrance aperture at the top of the housing. The fan duct may terminate at or near the fragrance aperture.

The flow altering mechanism may be adapted to facilitate spreading of the atomised fragrance into the surrounding environment.

The flow altering mechanism may be adapted to reduce fragrance residue building up on the dock or cartridge.

The cartridge may be disposable. The cartridge may be replaceable. Thus, a used cartridge may be removed from the electrical container and replaced with a fresh cartridge.

BRIEF DESCRIPTION OF THE DRAWINGS

In order that the invention may be more clearly understood and put into practical effect there shall now be described in detail preferred embodiments in accordance with the invention. The ensuing description is given by way of non-limitative examples only and is with reference to the accompanying drawings, wherein.

MODES FOR CARRYING OUT THE INVENTION

Figure 1:
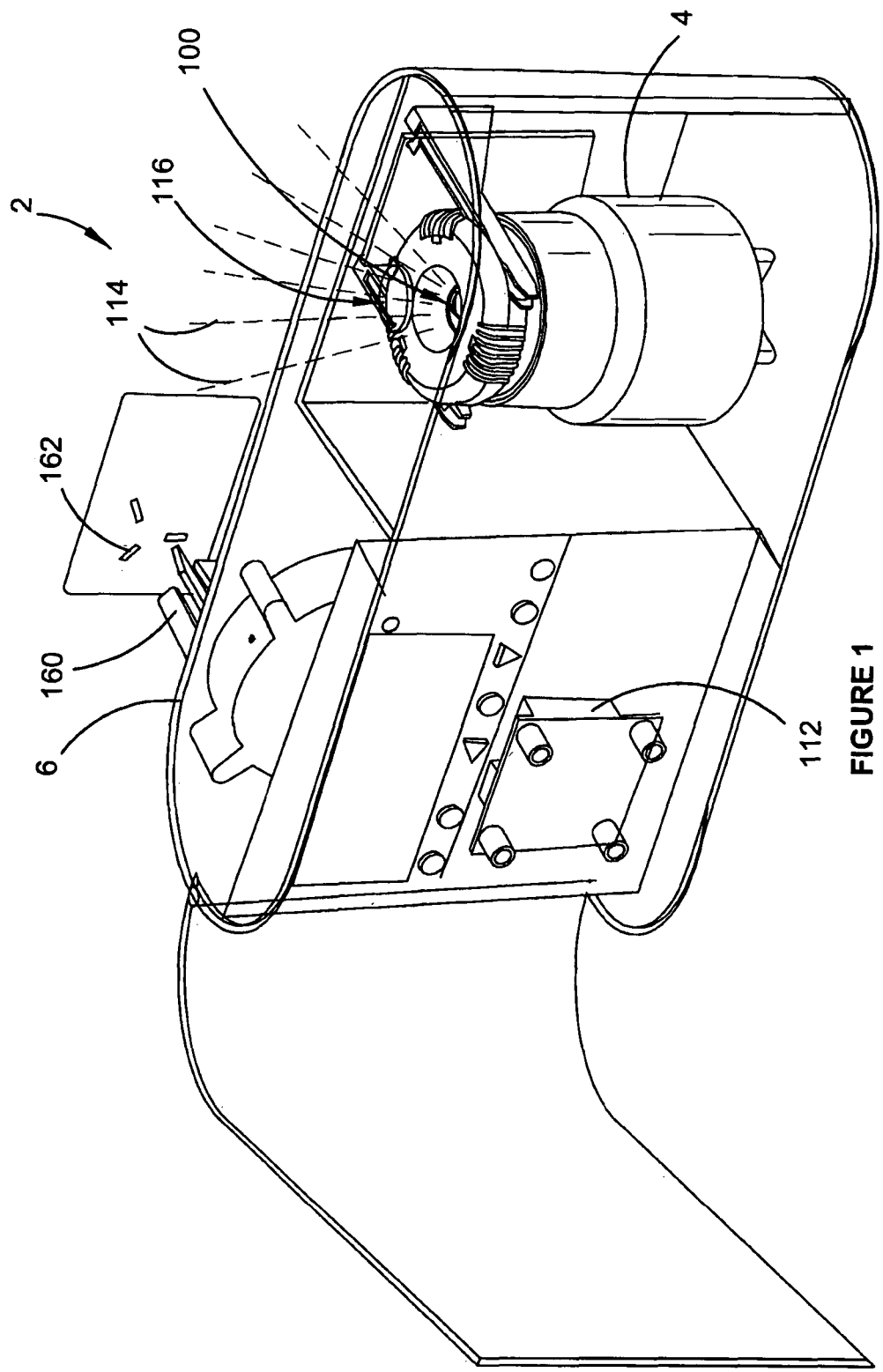
FIG. 1 is an open front perspective view of an atomiser system with a fragrance cartridge installed in a housing.

Referring to FIG. 1, there is shown an atomiser system, generally designated 2. The atomiser system comprises a fragrance cartridge 4 in a use configuration, and a docking housing 6 in which the fragrance cartridge 4 is installed.

The fragrance cartridge 4 in the drawings comprises:
a bottle 8 for holding a liquid fragrance 10 therein;
a liquid supply mechanism supported on top of, and extending down into, the bottle 8;
an atomising mechanism for atomising liquid fragrance 10 received from the liquid supply mechanism;
an electrical mechanism for connecting the atomising mechanism to a power source; and
an adjustment mechanism enabling adjustment of the cartridge 4 from a non-use configuration to a use configuration.

Figure 4:
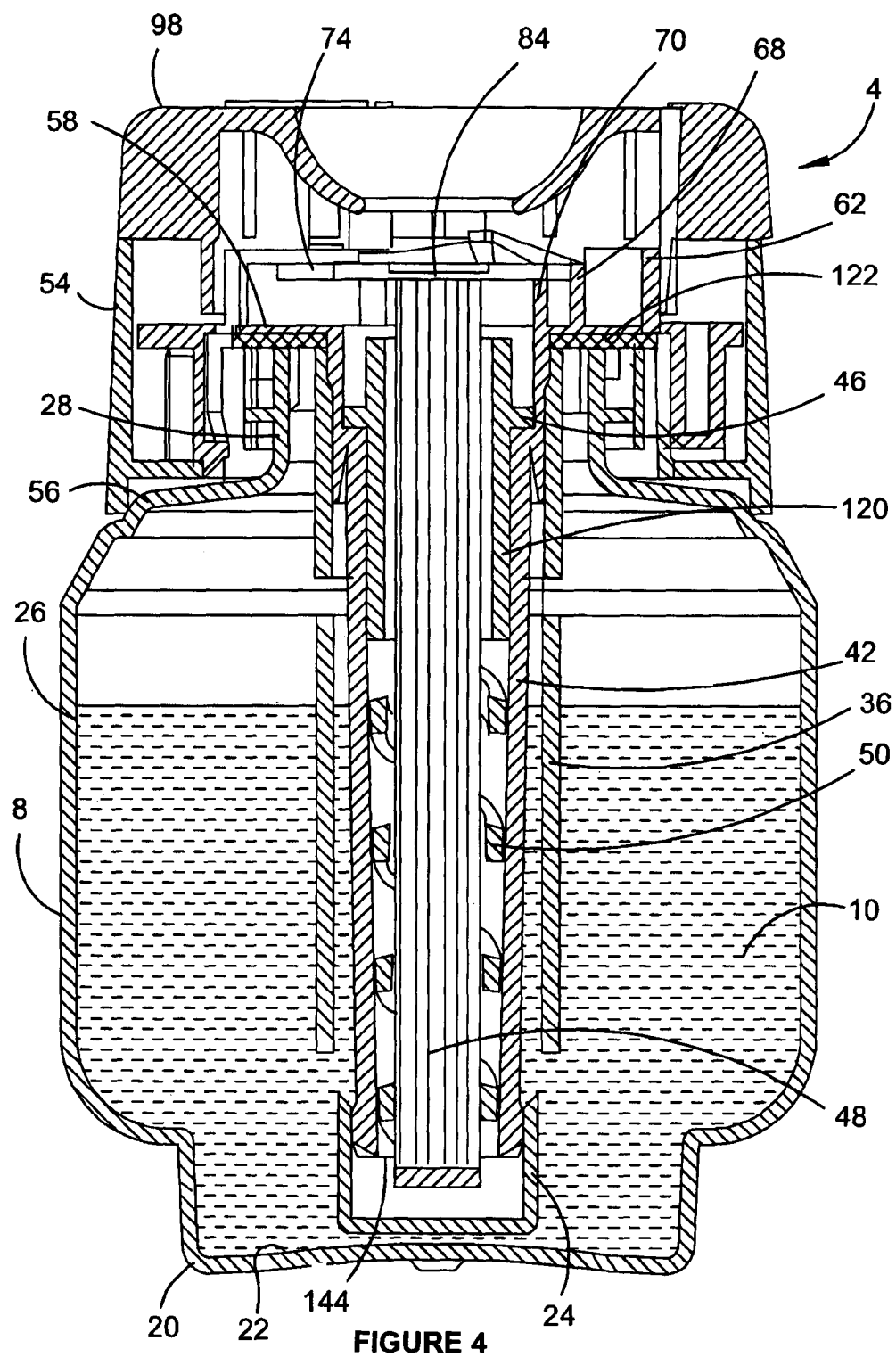
FIG. 4 is a front cut away view of the fragrance cartridge of FIG. 1 in a non-use configuration.
Figure 5:
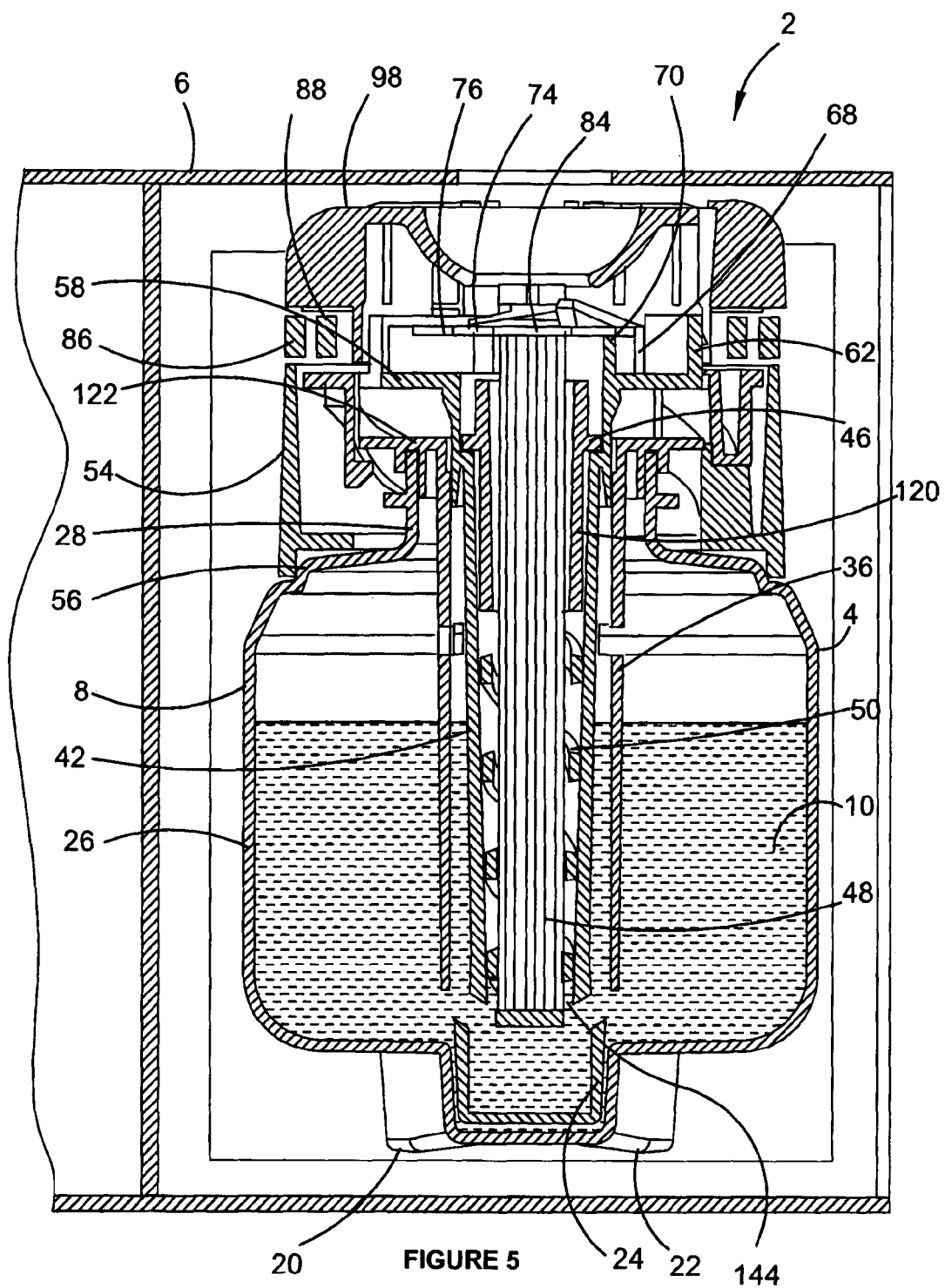
FIG. 5 is a front cut away view of the fragrance cartridge of FIG. 1 in a use configuration and mounted in the housing.
Figure 8:
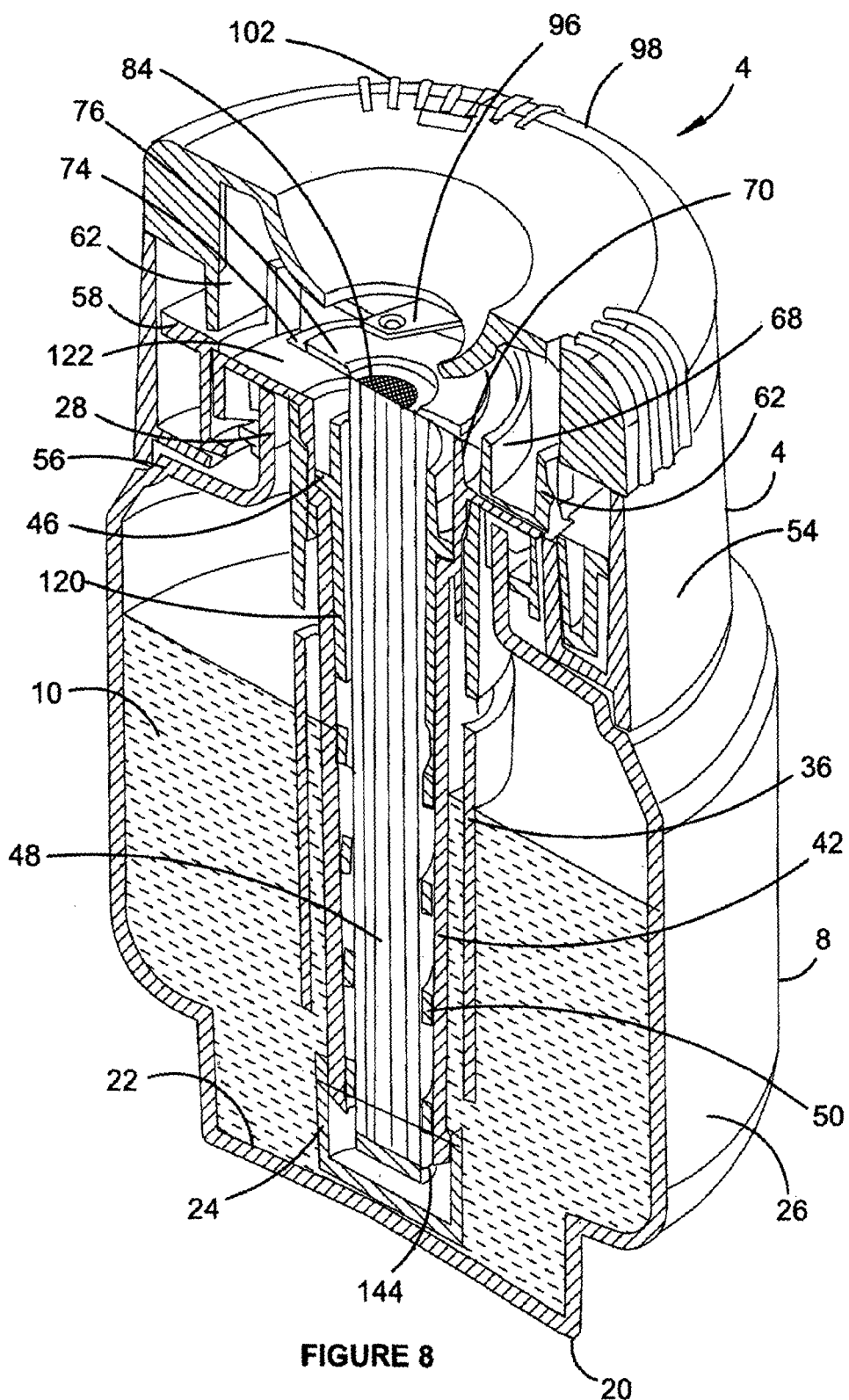
FIG. 8 is a front perspective cut away view from above showing the fragrance cartridge of FIG. 1 in a non-use configuration.
Figure 9:
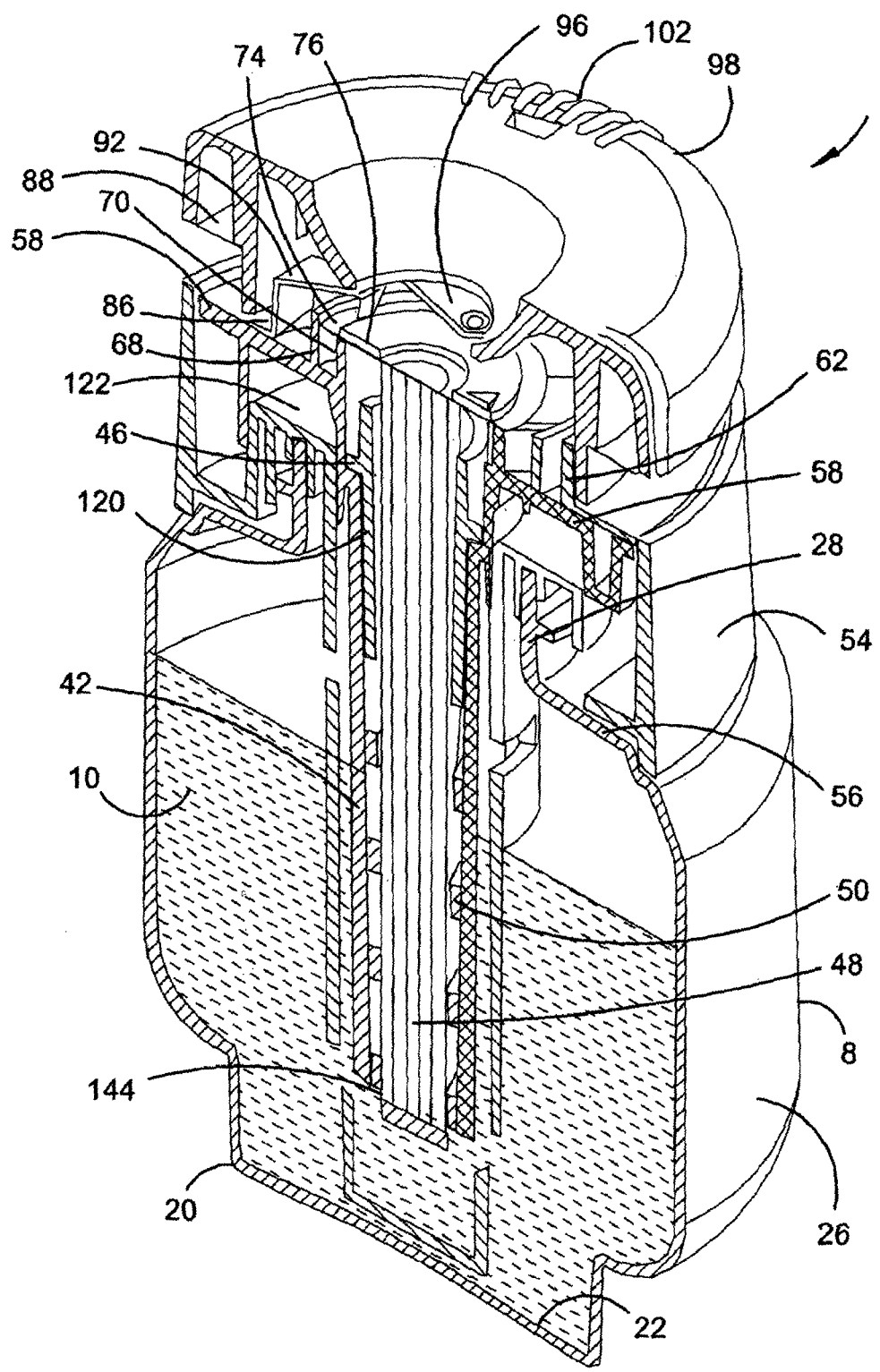
FIG. 9 is a front perspective cut away view from above showing the fragrance cartridge of FIG. 1 in a use configuration.
Figure 10:
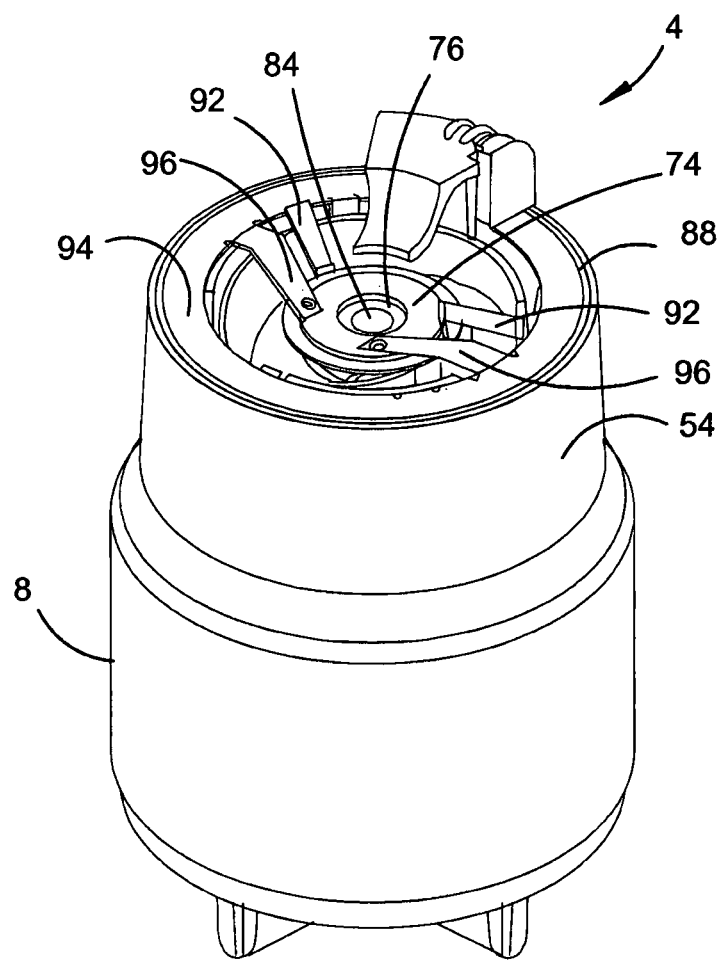
FIG. 10 is a perspective view from above of the fragrance cartridge with the cap mostly cut away, showing the arrangement of the piezo disc and electrical contacts when in a non-use configuration.
Figure 11:
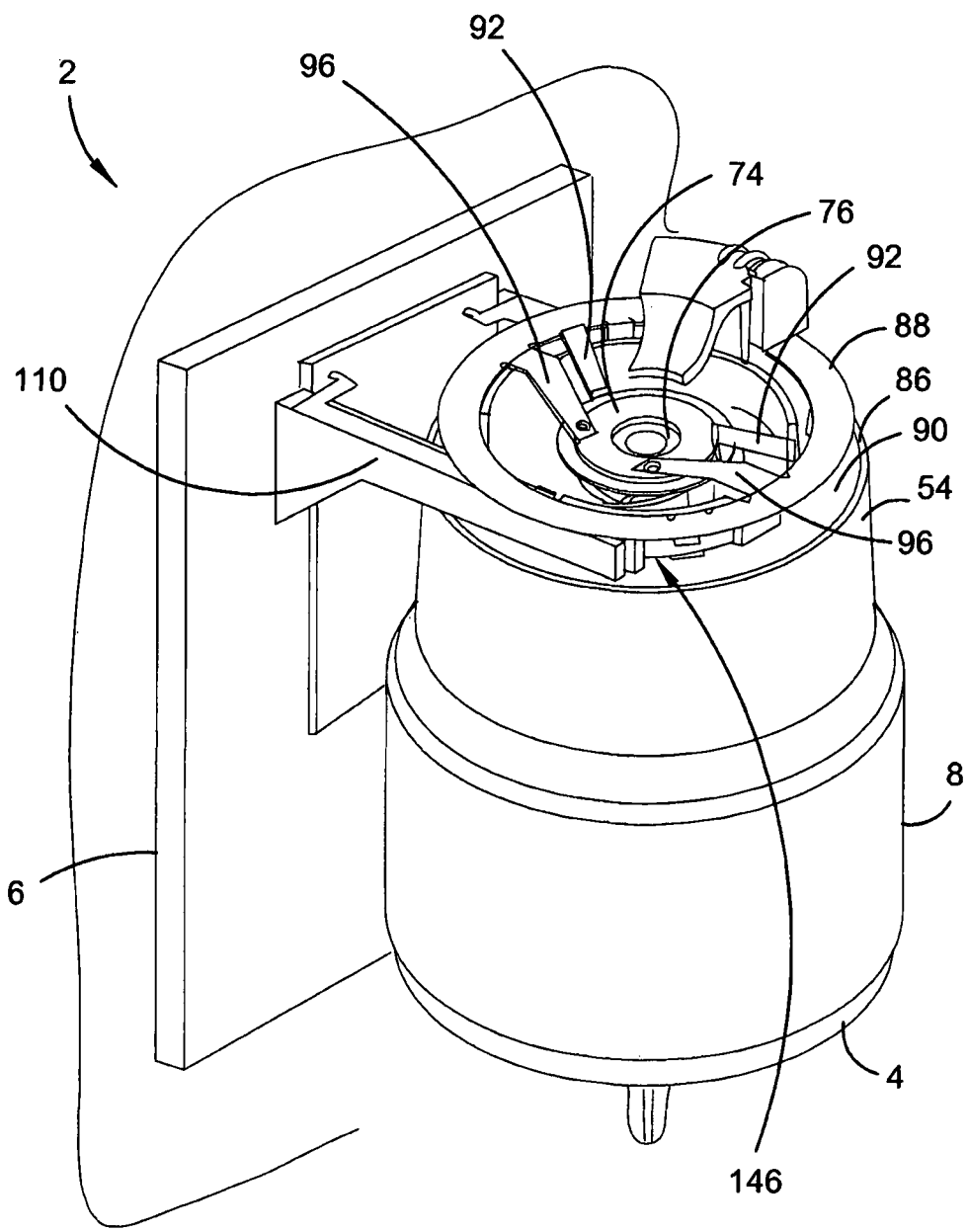
FIG. 11 is a perspective view from above of the fragrance cartridge with the cap mostly cut away, showing the arrangement of the piezo disc and electrical contacts when in a use configuration and mounted in the housing.

The bottle 8 comprises a base 20 having an X-shaped feeder trough 22 with a central circular feeder reservoir 24, although it is envisaged that feeder troughs of other shapes may be used in alternative embodiments. The reservoir 24 receives a lower part of the wicking mechanism when the cartridge is in the non-use configuration (see FIGS. 4 and 8). Above the base, the bottle 8 comprises a main reservoir 26 which communicates thereabove with a top inlet 28 which defines a top rim 30.

Figure 6:
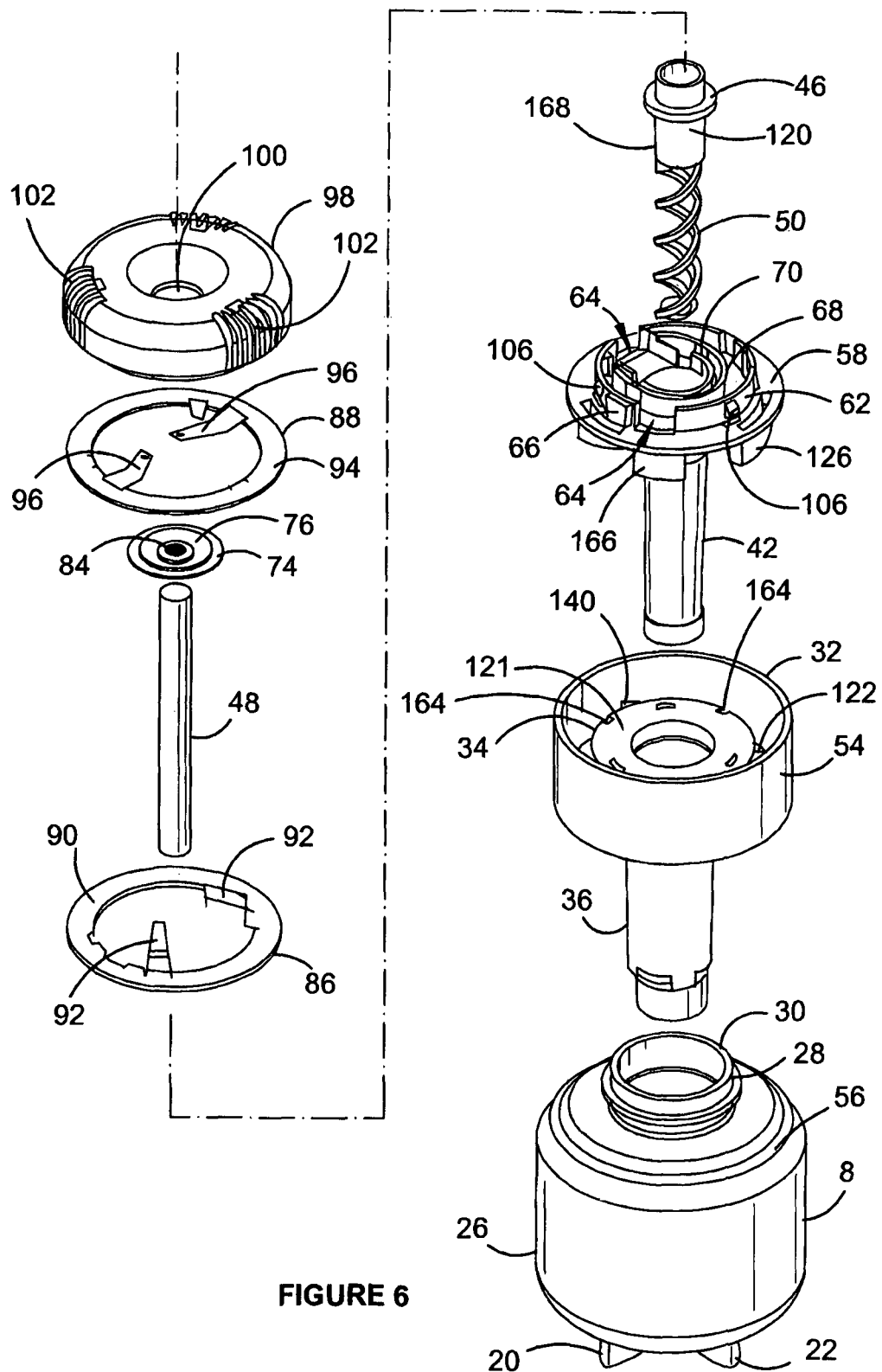
FIG. 6 is an exploded front perspective view showing the components of the fragrance cartridge of FIG. 1 from above.
Figure 7:
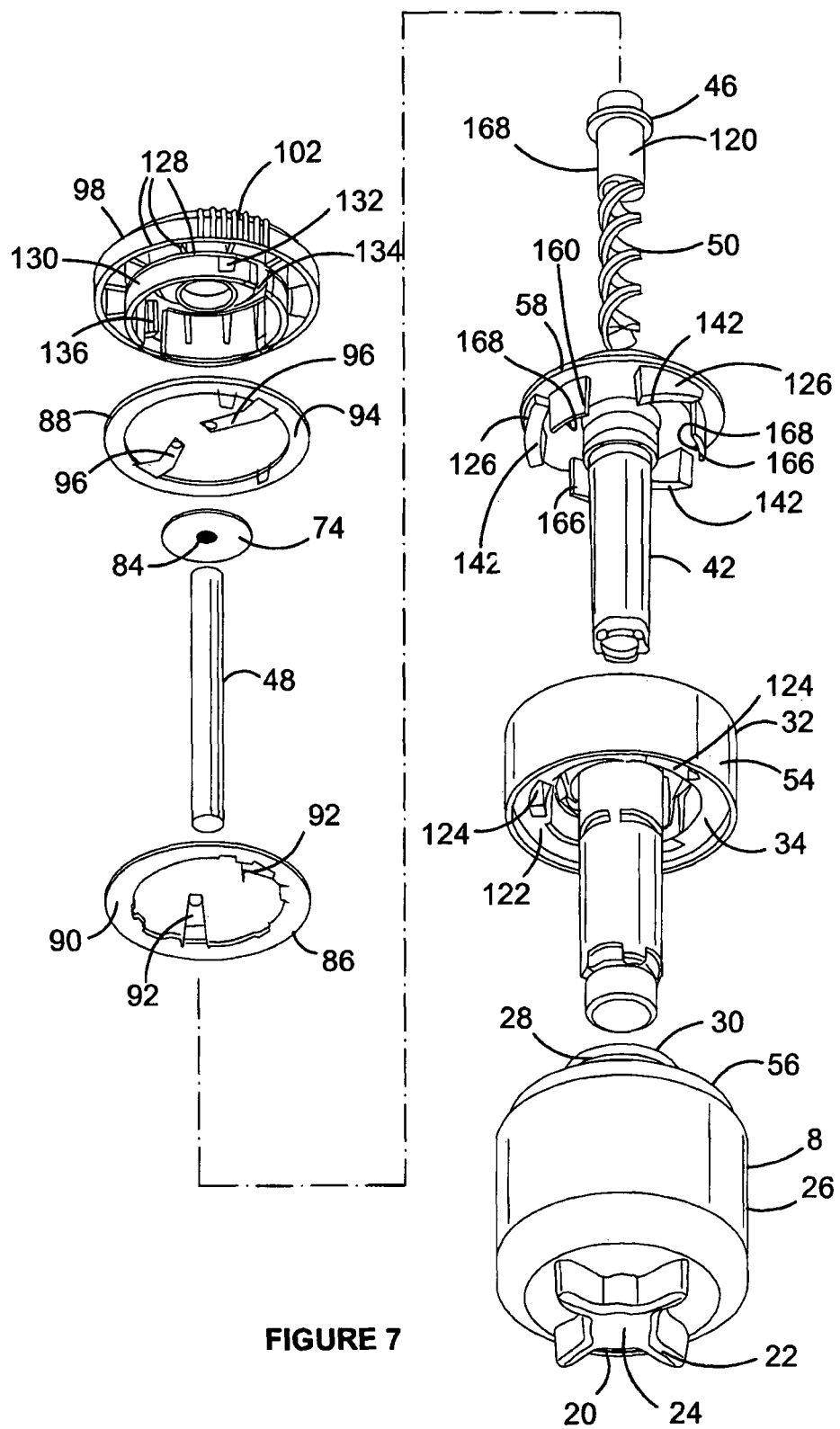
FIG. 7 is an exploded front perspective view showing the components of the fragrance cartridge of FIG. 1 from below.

The liquid supply mechanism comprises a bottle mount 32 (see FIGS. 6 and 7) which is mounted on the top rim 30 of the bottle and extends downwardly therein.

The bottle mount 32 comprises a top mounting portion 34 comprising an upper ledge 121 which is mounted on top rim 30 of the bottle, and a probe 36 which extends from the top mounting portion, down through the top inlet and main reservoir of the bottle, to just above the central reservoir 24 of the base 20. The probe 36 is tubular in shape with an open bottom end. Beneath the upper ledge 58, the top mounting portion 34 of the bottle mount 32 comprises a lower ledge 122. The lower ledge has a plurality of slots 124 and adjustment ramps 140 which ramp up from an end of respective slots 124. Guide slots 164 are also present in the bottle mount 32 adjacent the ramps 140. The guide slots have the same angle of inclination as the ramps in the embodiment shown (see FIGS. 6, 17 & 18).

The bottle mount 32 further comprises a collar 54 which is aligned above but does not contact a bottle ledge 56 of the bottle 8. The collar surrounds the top inlet 28 of the bottle 8 and the top mounting portion 34 of the bottle mount.

The liquid supply mechanism further comprises a holding member having an elongated tubular shaped outer wick holder 42 which extends down through the probe 36 of the bottle mount 32. When in the non-use configuration, the bottom of the outer wick holder 42 protrudes through and beyond the open bottom end of the probe 36 and into the central reservoir 24 of the base 20 (see FIGS. 4 and 8).

At the top end of the outer wick holder 42, the holding member comprises a flat horizontal circular ring 58. Projecting upwardly from the flat circular ring 58 is a rounded outer wall 62 defining a pair of square ways 64. The rounded outer wall 62 also has a pair of central square steps 66 jutting out from opposite sides of the wall 62.

A rounded intermediate wall 68 also projects upwardly from the flat circular ring 58 within the bounds of outer wall 62. Inside the intermediate wall 68, a curved inner wall 70 projects upwardly from the flat circular ring 58 along its inner circumference. A plurality of adjustment members 126 of various shapes and sizes, and with a curved bottom surface 142, project downwardly from the circular ring 58 and onto corresponding ramps 140 of the bottle mount 32 (see FIGS. 7, 17, & 18). Also projecting downwardly from the circular ring 58 adjacent the adjustment members is a plurality of ribs 166. Each rib has an inwardly projecting guide pin 168 which is engaged in a corresponding guide slot 164.

The liquid supply mechanism further comprises an elongated wick 48 which is adapted to draw in the liquid fragrance (when the cartridge is in the use configuration) and move the fragrance along to dry areas of the wick via capillary action. The wick 48 extends lengthwise within the outer wick holder 42.

The liquid supply mechanism further comprises an inner wick holder comprising a plastic spring 50 which surrounds a portion of the wick 48 in the probe 36. The spring extends downwardly from a top member 120 to the base of the outer wick holder 42. The top member 120 has an external ridge 46 for abutment against an internal support collar towards the top of the outer wick holder, thereby supporting and limiting downward translation of the spring 50 and top member 120 in the outer wick holder 42.

The atomising mechanism comprises a piezo stainless steel mesh sheet 74 and a piezo ceramic ring 76 mounted thereon. In the embodiment shown in FIGS. 1 to 13, the piezo sheet 74 and ring 76 are arranged centrally and perpendicularly with respect to the length of the wick. A circular central perforated portion 84 of the piezo sheet 74 is in contact with the top of the wick 48 and allows passage of fragrance particles therethrough.

Figure 14:
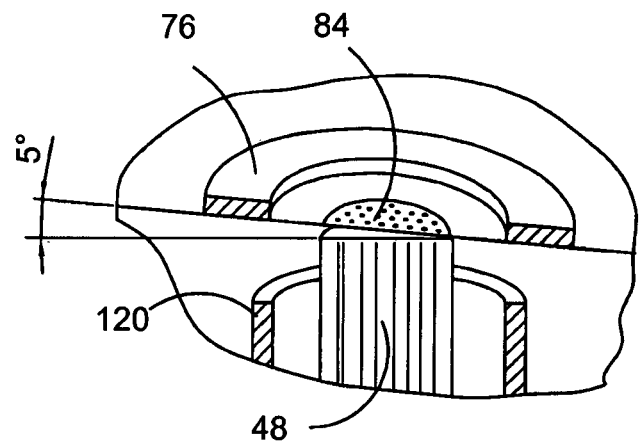
FIG. 14 is a close up view of the wick and piezo disc, showing the disc mounted 5 degrees off-perpendicular to the longitudinal axis of the wick.
Figure 15:
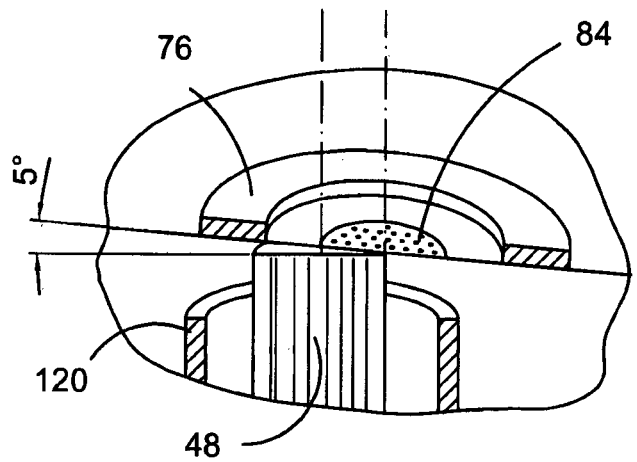
FIG. 15 is a close up view of the wick and piezo disc, showing the disc mounted off centre and angled to the longitudinal axis of the wick.

It is envisaged, however, that in other embodiments the piezo sheet 74 and ring 76 may be arranged at an angle, such as about 5 degrees, off perpendicular to the vertically aligned wick 48 (see FIG. 14). Additionally or alternatively, the piezo sheet 74 and ring may be arranged off centre with respect to the top of the wick (see FIG. 15). These off centre and/or angled arrangements regulate supply of liquid fragrance from the wick 48 to the piezo ring 76, thereby limiting the risk of water logging and degradation of the disc. Water logging or oversaturation can cause either excessive emission of atomised fragrance particles due to oversupply of liquid fragrance, or a reduction or cessation in emission due to inhibition of small liquid particles being diffused or thrown off the piezo disc.

As shown clearly in FIGS. 6, 7, 10 and 11, the electrical mechanism comprises a bottom contact 86 and a top contact 88, which are both made of an electrically conductive material.

The bottom contact 86 has a flat contact ring 90 and a pair of contact arms 92. The contact arms pass through respective square ways 64 in outer wall 62 and extend inwardly to contact the piezo mount 74, thereby providing an electrical connection to the piezo disc 76.

The top contact also has a flat contact ring 94 and contact arms 96. The contact arms 96 extend inwardly over the central square steps 66 of the outer wall 62 to the piezo mount 74, where they provide an electrical connection for the piezo disc 76.

The adjustment mechanism comprises a circular cap 98 having a central aperture 100 which overlies the perforations 84 in the piezo mount, enabling passage of atomised particles therethrough.

The circular cap 98 comprises gripping ridges 102 on its external surface to facilitate cap adjustment by the user. A strutted circumferential outer double wall 128 can be seen on viewing the underside of the cap 98.

Projecting downwardly from within the strutted wall 128 is a circular connection wall 130 having notches 132 which are adapted to receive corresponding tabs 106 projecting from rounded outer wall 62 of the holding member, thereby connecting the cap 98 to the holding member.

A pair of opposed rectangular step slots 134 forms a break in the connection wall 130. These step slots 134 provide a space for corresponding steps 66 of the rounded outer wall 62 of the holding member. Step abutment members 136 project into the upper space of the step slots 134 and rest atop the steps 66.

The fragrance cartridge is adjustable from a non-use configuration as shown in FIGS. 2, 4, 8, 10 and 17 to a use configuration as shown in FIGS. 1, 3, 5, 9, 11 and 18.

In the non-use configuration, the cap 98, electrical mechanism, atomising mechanism, outer wick holder 42, top member 120, and wick 48 are in a downwardly depressed position with respect to the bottle mount 32 and bottle 8. In this depressed position, the collar 54 of the bottle mount 32 closes off external access to the top and bottom electrical contacts, 88 and 86 respectively, so that the piezo disc 76 is unable to be connected to an external electrical power source.

Further, in the depressed position, the wick 48, top member 120, and outer wick holder 42 project down through the bottom aperture of the bottle mount 32 and into the central circular feeder reservoir 24 of the base 20 of the bottle 8. This arrangement blocks access of the liquid fragrance 10 to the wick 48 through opening 144, thereby keeping the piezo disc 76 dry until use of the cartridge is required.

Figure 2:
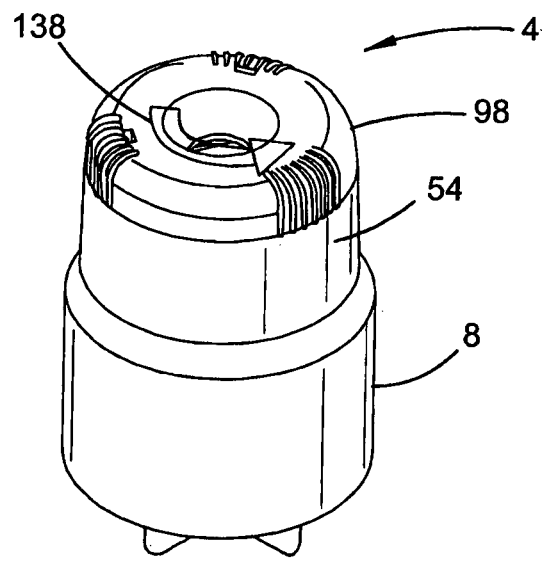
FIG. 2 is a front perspective view of the fragrance cartridge of FIG. 1 in a non-use configuration prior to installation in the housing.
Figure 17:
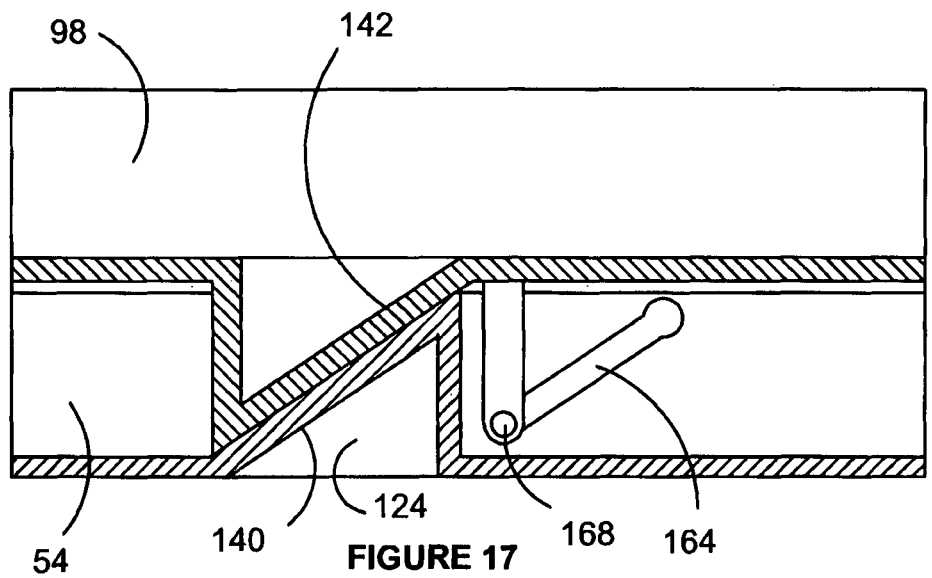
FIG. 17 is a diagrammatic view showing a pair of articulating ramps next to a guide slot with pin when in a non-use configuration.
Figure 18:
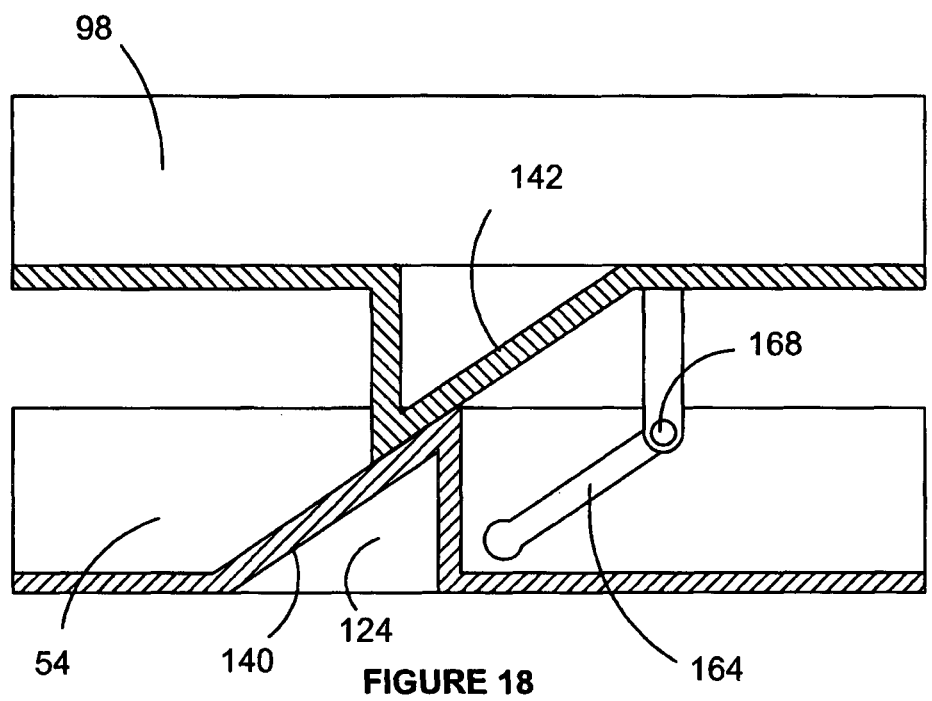
FIG. 18 is a diagrammatic view showing a pair of articulating ramps next to a guide slot with pin when in a use configuration.
Figure 19:
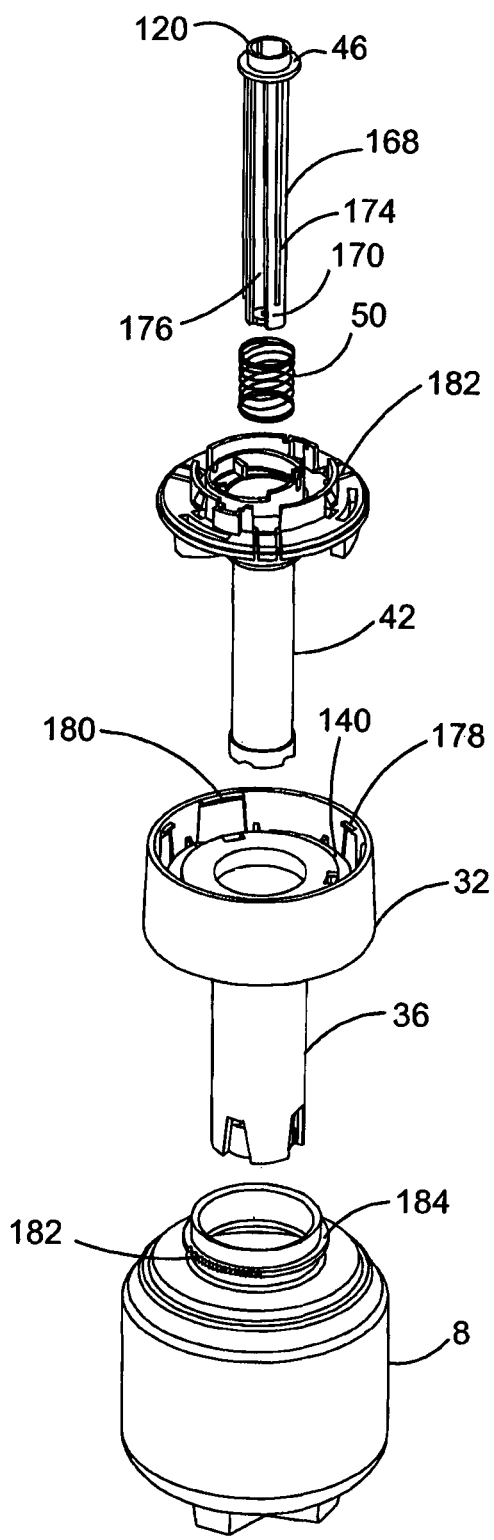
FIG. 19 is an exploded front perspective view showing the components of alternative form of fragrance cartridge from above.
Figure 20:
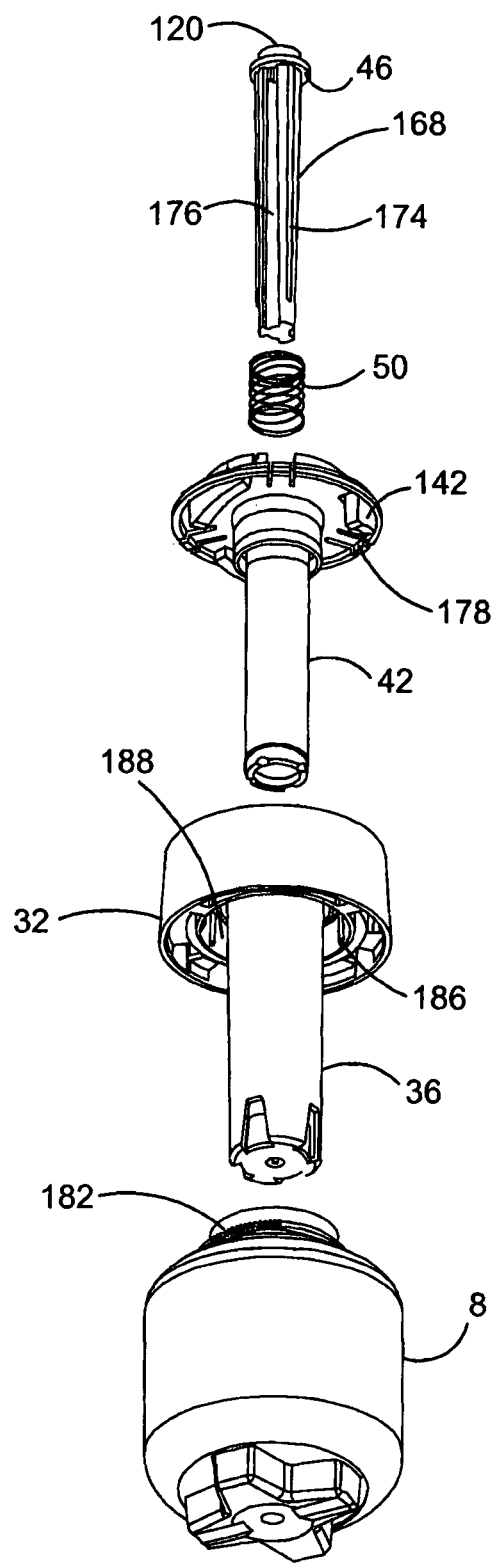
FIG. 20 an exploded front perspective view showing the components of the alternative form of fragrance cartridge from below.

Twisting the cap 98 with sufficient force in an anticlockwise direction, as indicated by arrow 138 in FIG. 2, causes the bottom surface 142 of adjustment members 126 to slide up respective adjustment ramps 140, and concomitantly the guide pins 168 to slide up along respective guide slots 164, thereby releasing and raising the holding member from the bottle mount 32 (see FIGS. 17 & 18). Thus, the cap 98, top contact 88, bottom contact 86, piezo mount 74 with disc 76, wick 48, spring 50, top member 120, and holding member with outer wick holder 42 rise up with respect to the bottle mount 32 and bottle 8.

This upward displacement brings the cartridge 4 into a use configuration whereby top and bottom electrical contacts, 86 and 88 respectively, are accessible above the level of the collar 54. Further, the outer wick holder 42 is raised up out of the dry central reservoir 24, enabling liquid fragrance to flow into the reservoir 24 and around the base of the outer wick holder 42 which has openings 144 enabling the liquid fragrance to access the wick. The liquid fragrance is then drawn up through the wick by capillary action to the piezo disc 76, thereby wetting the disc with the liquid fragrance 10.

The arrangement is such that, once in the use configuration, the surface area of the wick in contact with the liquid fragrance remains substantially constant throughout the life of the cartridge, regardless of the level or amount of the liquid fragrance in the bottle, or of the orientation of the bottle. This enables substantially consistent supply of the liquid fragrance via the wick to the piezo disk throughout the life of the cartridge.

Due to a vacuum effect created in the closed bottle, as the liquid fragrance is transported up from the bottle reservoir to the piezo disc via capillary action of the wick, an air bubble is sucked from the probe space surrounding the wick into the bottle reservoir. This vacuum effect prevents the liquid from passing into the probe space surrounding the wick, thereby ensuring the surface are of the wick in contact with the liquid remains unchanged.

Figure 3:
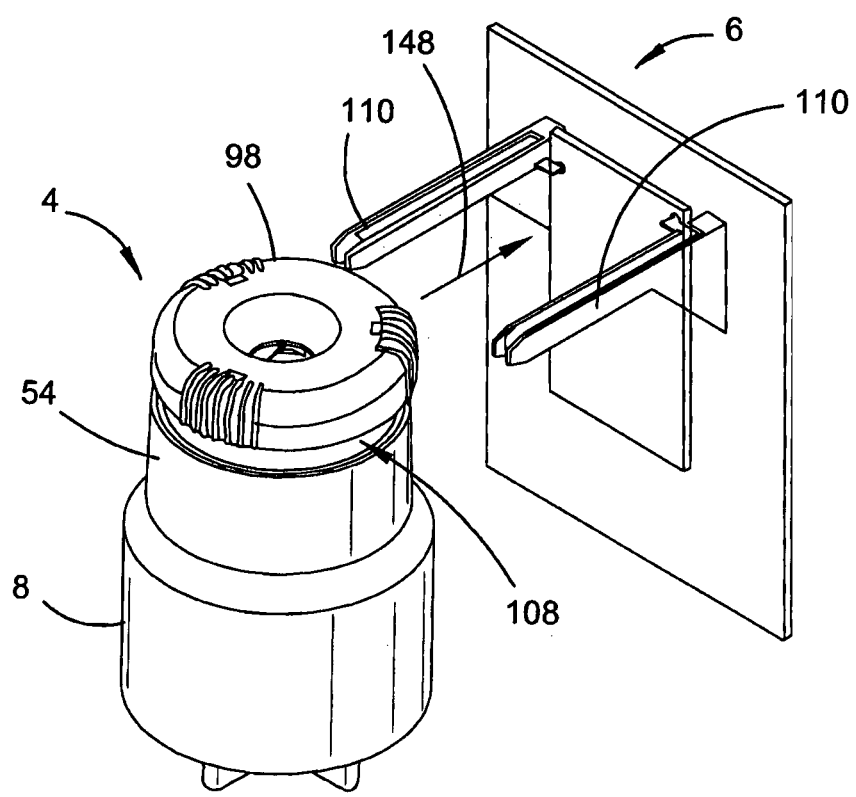
FIG. 3 is a front perspective view of the fragrance cartridge of FIG. 1 in a use configuration and ready for mounting in the housing.

As shown in FIG. 3, the gap 108 created between the cap 98 and collar 54 provides space for the cartridge to be placed between (as indicated by arrow 148) and retained by a pair of electrical retention arms 110 of the docking housing 6.

Figure 12:
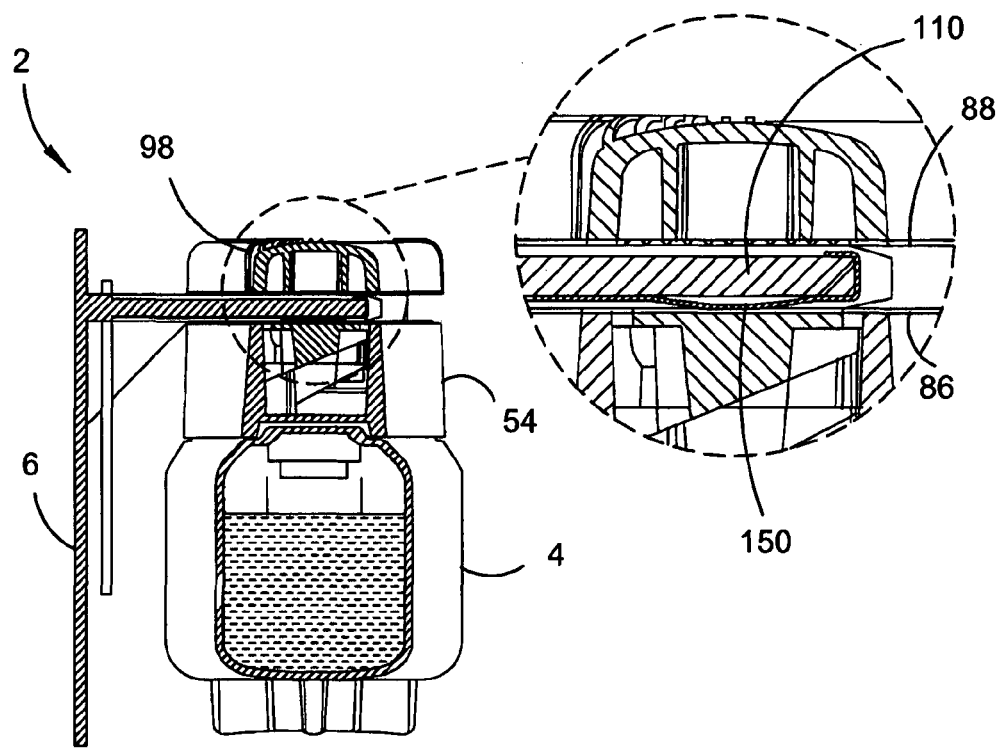
FIG. 12 is a right side view of the atomiser system, with the cartridge partially cut away and the encircled region magnified in the inset, showing the right prong of the electrical dock contacting the bottom electrical contact of the fragrance cartridge.
Figure 13:
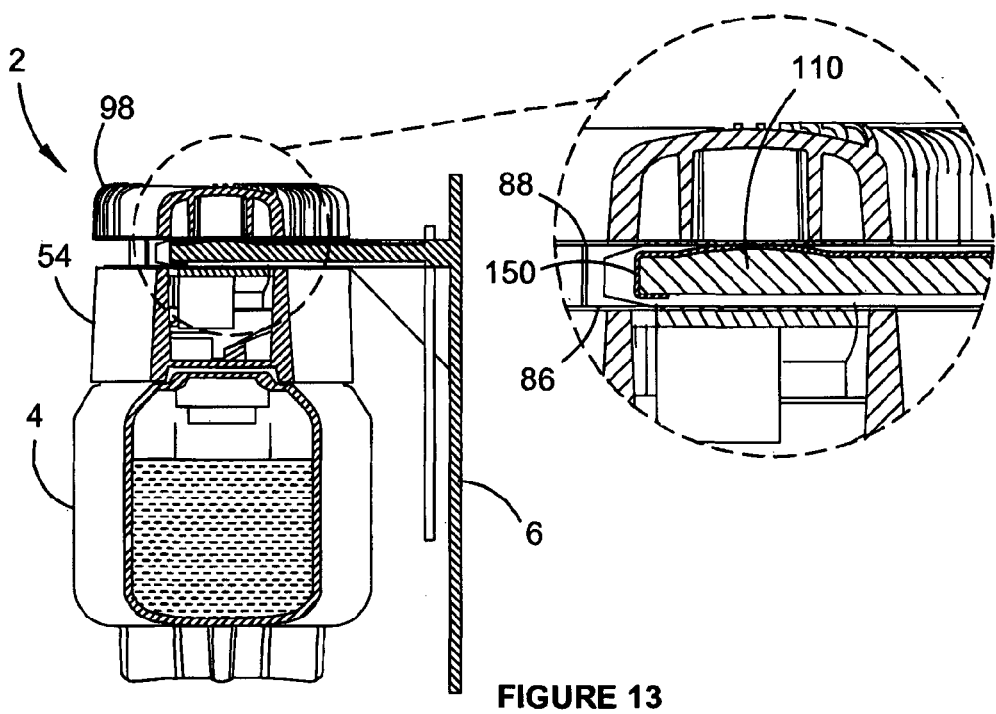
FIG. 13 is a left side view of the atomiser system, with the cartridge partially cut away and the encircled region magnified in the inset, showing the left prong of the electrical dock contacting the top electrical contact of the fragrance cartridge.

The inset of FIG. 12 illustrates how electrical wiring 150 extends out from the housing along the undersurface of the right electrical retention arm 110, dipping down to contact the bottom contact 86 before wrapping up and around the end of the right retention arm. Similarly, the inset of FIG. 13 illustrates how electrical wiring 150 extends out from the housing along the topsurface of the left electrical retention arm 110, rising up to contact the top contact 88 before wrapping down and around the end of the left retention arm.

The docking housing 6 has a Piezo driver 112 from which energy is transmitted through the electrical wiring 150, electrical retention arms 110 and electrical mechanism to the piezo disc 76. This causes the wet piezo disc 76 to vibrate rapidly, thereby causing atomised fragrance particles 114 to be thrown off up through the central aperture 100, and through a corresponding fragrance aperture 116 at the top of the housing and into the surrounding air.

It is envisaged that the mains power supply will be the electrical power source, with prongs 160 of the cartridge or housing adapted for plugging into an electrical wall socket connected with the mains. In alternative forms of the invention, it is envisaged that the docking housing or the cartridge comprises its own internal battery.

Figure 16:
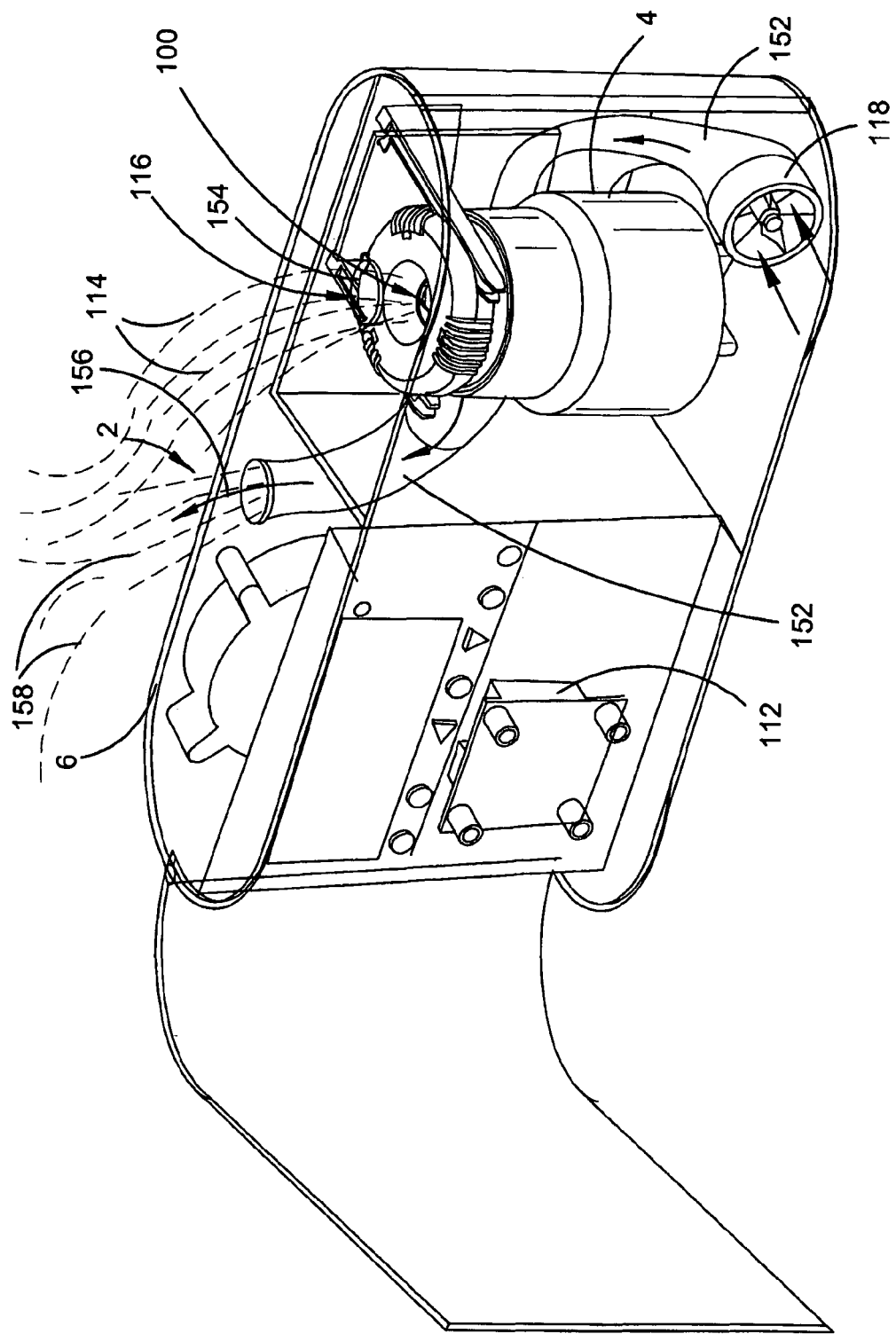
FIG. 16 is an open front perspective view of an atomiser system having a fan duct configuration for enhancing spreading of fragrance into the external environment.

In FIG. 16, the docking housing 6 has a flow altering mechanism comprising a fan duct 152, a turbine 118 at one end of the fan duct 152, and an air aperture 154 at the other end of the fan duct, the duct exit opening 154 being present in the top of the housing 6 adjacent the fragrance aperture 116.

As indicated by arrows 156, spinning of turbine 118 causes air 158 to be drawn into the duct 152 at the turbine end, up through the duct, and out through the air aperture 154 to the external environment. This flow of air 158 out through opening 154 creates a venturi effect due to pressure difference adjacent aperture 116 which causes the emitted mist fragrance 114 to be drawn toward the air flow, thereby improving spreading of the fragrance into the external environment whilst limiting build-up of fragrance residue on top of the housing 6.

When the cartridge 4 runs out of liquid fragrance 10 it may be removed from the housing 6 and disposed of. A fresh replacement cartridge may then be unlocked to its use configuration and installed in the housing 6 for further use.

While this invention has been described in connection with specific embodiments thereof, it will be understood that it is capable of further modification(s). The present invention is intended to cover any variations, uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the broad consistory statements. Various modifications and equivalent arrangements are intended to be included within the spirit and scope of the invention and consistory statements herein. Therefore, the specific embodiments are to be understood to be illustrative of the many ways in which the principles of the present invention may be practiced.

For example, in the form described above, the amount of twisting of the cap 98 is limited by the guide pins 168 abutting against the ends of respective guide slots 164. However, in the alternative embodiment shown in FIGS. 19 and 20, ramps 140 and 142 remain present, but ribs 166, guide pins 168 and guide slots 164 are omitted and instead

- three first flexible ridge features 178 have been added to bottle mount 32, the first ridge features 178 being adapted to prevent pushing back into the non-use configuration following activation;
- three second flexible ridge features 180 have been added to bottle mount 32, the second flexible ridge features being adapted to prevent removal of the cap 98 whilst allowing free rotation thereof following cartridge activation;
- twelve vertical teeth 186 have been added to inward facing circular wall 188 of the bottle mount 32; and
- a pair of opposed sets of fifteen teeth 182 have been incorporated into external rim 184 of the top inlet 28 of bottle 8, the teeth 182 being adapted to limit rotation of the bottle mount 32 on bottle 8 by virtue of abutment against vertical teeth 182.

Further illustrated in FIGS. 19 and 20 is an alternative form of inner wick holder 168. The alternative inner wick holder 168 comprises a tube 170 in which the wick is held. The tube 170 extends downwardly from top member 120, has three spaced longitudinal ridges 174, and defines three spaced longitudinal channels 176. In this embodiment, the spring 50 is separate to, rather than a part of, the inner wick holder 168. Further, the spring 50 is made of metal rather than plastic. The bottom of spring 50 may sit atop the internal support collar of the outer wick holder 42, whilst the the top of the spring 50 may abut against the undersurface of the external ridge 46 of the top member 120.

Where the terms “comprise”, “comprises”, “comprised” or “comprising” are used in this specification, they are to be interpreted as specifying the presence of the stated features, integers, steps or components referred to, but not to preclude the presence or addition of one or more other features, integers, steps, components to be grouped therewith.

The invention claimed is:

1. An atomiser system comprising:

a cartridge comprising:

a container to contain a liquid, an atomiser to atomise the liquid, the atomiser comprising a piezo disc, an electrical contact to electrically connect the atomiser to an electrical power source, the cartridge being adjustable to alter or maintain a wetness of the piezo disc.

2. The atomiser system according to claim 1 wherein the cartridge is adjustable between a dry configuration in which the piezo disc is or becomes substantially dry of the liquid, and a wet configuration in which the piezo disc is or becomes wet with the liquid.

3. The atomiser system according to claim 2 wherein in the dry configuration a supply of liquid to the piezo disc is inhibited, and in the wet configuration the supply of liquid to the piezo disc is enabled.

4. The atomiser system according to claim 1 wherein the piezo disc is to remain dry until the cartridge is activated by a user.

5. The atomiser system according to claim 1 wherein the system is structured to maintain the piezo disc at a substantially consistent wetness despite changes in cartridge orientation or liquid volume in the container.

6. The atomiser system according to claim 1 further comprising a wick to supply the liquid to the piezo disc, the cartridge being adjustable to alter the supply of liquid to the piezo disc.

7. The atomiser system according to claim 6 wherein the wick is to draw the liquid therealong, the wick being in contact with the piezo disc.

8. The atomiser system according to claim 7 wherein, when the wick is exposed to the liquid, a surface area of the wick in contact with the liquid remains substantially the same regardless of an amount of liquid remaining in the container or an orientation of the cartridge.

9. The atomiser system according to claim 7 further comprising a spring biased to urge a part of the wick against the piezo disc.

10. The atomiser system according to claim 7 wherein the wick is adjustable between a first configuration in which the wick is separated from the liquid, and a second configuration in which a part of the wick is in contact with the liquid.

11. The atomiser system according to claim 7 wherein the piezo disc is to contact an end of the wick at an angle rather than flatly.

12. The atomiser system according to claim 11 wherein the piezo disc is angled between 1 and 10 degrees with respect to the end of the wick.

13. The atomiser system according to claim 7 wherein the piezo disc contacts an end of the wick off centre.

14. The atomiser system according to claim 1 further comprising an adjustable cap, the wetness of the piezo disc being alterable by adjustment of the cap.

15. The atomiser system according to claim 1 wherein the electrical power source is external to the cartridge, and the cartridge is adjustable between a first configuration in which the electrical contact is inhibited from electrically connecting the atomiser to the electrical power source, and a second configuration in which the electrical contact is accessible for electrical connection of the atomiser to the electrical power source.

16. The atomiser system according to claim 1 wherein the cartridge is to emit atomised liquid particles in any cartridge orientation.

17. The atomiser system according to claim 1 further comprising a dock for the cartridge.

18. The atomiser system according to claim 17 wherein the dock comprises an electrical retainer, the electrical retainer to removably retain the cartridge in the dock, and electrically connect the retained cartridge to the power source.

19. The atomiser system according to claim 17 wherein the dock comprises a turbine to alter a flow path of atomised particles as they are emitted from the system.

20. The atomiser system according to claim 19 wherein the turbine is to generate an external air flow adjacent the atomised particles of the liquid as they are emitted from the cartridge or dock, thereby drawing the emitted particles toward the external air flow.

* * * * *